(12) United States Patent
Kim et al.

(10) Patent No.: US 10,245,292 B2
(45) Date of Patent: Apr. 2, 2019

(54) COMPOSITION FOR ENHANCING MALE SEX HORMONE AND MEN'S HEALTH

(71) Applicant: FAMENITY CO., LTD., Gwacheon-si, Gyeonggi-do (KR)

(72) Inventors: Do Hee Kim, Seoul (KR); Yoon Hwa Jeong, Yongin-si (KR); Ji Won Lee, Gwacheon-si (KR); Yoo Hun Noh, Seoul (KR); Ji Ae Park, Seoul (KR); Seng Ah Lee, Gwangmyeong-si (KR)

(73) Assignee: FAMENITY CO., LTD, Gwacheon-si (KR)

( * ) Notice: Subject to any disclaimer, the term of this patent is extended or adjusted under 35 U.S.C. 154(b) by 417 days.

(21) Appl. No.: 14/819,441

(22) Filed: Aug. 6, 2015

(65) Prior Publication Data
US 2015/0335694 A1    Nov. 26, 2015

Related U.S. Application Data

(63) Continuation of application No. PCT/KR2013/012124, filed on Dec. 24, 2013.

(30) Foreign Application Priority Data

Feb. 8, 2013 (KR) ........................ 10-2013-0014407

(51) Int. Cl.
| | | |
|---|---|---|
| *A61K 36/288* | (2006.01) | |
| *A61K 36/48* | (2006.01) | |
| *A23L 33/00* | (2016.01) | |
| *A23L 33/10* | (2016.01) | |
| *A23L 33/105* | (2016.01) | |

(52) U.S. Cl.
CPC ............ *A61K 36/288* (2013.01); *A23L 33/00* (2016.08); *A23L 33/10* (2016.08); *A23L 33/105* (2016.08); *A23L 33/30* (2016.08); *A61K 36/48* (2013.01); *A23V 2002/00* (2013.01); *A61K 2236/37* (2013.01); *A61K 2236/51* (2013.01)

(58) Field of Classification Search
None
See application file for complete search history.

(56) References Cited

U.S. PATENT DOCUMENTS

2010/0255127 A1 * 10/2010 Norimoto .............. A61K 36/00
424/729

FOREIGN PATENT DOCUMENTS

| JP | 06-211682 A | | 8/1994 |
| KR | 20110042487 A | * | 4/2011 |
| KR | 20110058398 A | * | 6/2011 |

OTHER PUBLICATIONS

Noh et al. Nutrition Research and Practice (Nutr Res Pract);6(6):505-512 (Year: 2012).*

* cited by examiner

*Primary Examiner* — Amy L Clark
(74) *Attorney, Agent, or Firm* — STIP Law Group, LLC

(57) ABSTRACT

The present disclosure relates to a use of a dandelion extract and a Rooibos extract. The present disclosure also relates to a food composition and a pharmaceutical composition for preventing and improving climacteric, including a dandelion extract, or a dandelion and Rooibos composite extract as an active ingredient.

5 Claims, 11 Drawing Sheets

COMPOSITION FOR ENHANCING MALE SEX HORMONE AND MEN'S HEALTH

CROSS-REFERENCE TO RELATED APPLICATIONS

The present application is a continuation of International Patent Application No. PCT/KR2013/012124, filed Dec. 24, 2013, which is based upon and claims the benefit of priority to Korean Patent Application No. 10-2013-0014407, filed on Feb. 8, 2013. The disclosures of the above-listed applications are hereby incorporated by reference herein in their entirety.

TECHNICAL FIELD

The present disclosure has been achieved by Project No. A085138 under the support of the Ministry of Health, Welfare, and Family Affairs, Republic of Korea. The main organization in charge of R&D of the project was Korea Health Industry Development Institute, R&D Business Name was "Business of Healthcare Development", R&D Project Name was "Special R&D Center for Urogenital Diseases", the Managing Organization was CHUNG ANG University industry Academic Cooperation Foundation, and the R&D Period was between Apr. 1, 2008 and Mar. 31, 2013.

BACKGROUND ART

Dandelion is a perennial plant belonging to Family Asteraceae, and the dried entire plant called *Taraxacum mongolicum* is used as a drug in herbal medicine. Dandelion has been used in folk or herbal medicine for the purpose of anti-inflammation, stamina, fever release, dieresis, strengthening stomach, phlegm discharge, detoxication, and the like, even in western world, has been used as drugs for promoting bile secretion, anti-rheumatism, diuresis, and the like. Additionally, "Bencao Zhenyi" describes that dandelion has therapeutic effects for the treatment of heat toxin, reddish swelling, pus, and suppuration due to its cool property, and can be orally administered or used for external application. However, the effect of dandelion on prevention or improvement of male climacteric has not been studied. Rooibos is a conifer native to only highlands of Cape of Good Hope, South Africa, and has therapeutic effects of improving various kinds of skin diseases, allergy symptoms (treatment of various atopic dermatitis, and the like.), normalizing blood pressure, improvement of diabetes, constipation relief and regulation of intestinal regulation, anti-aging, mental stability, dieresis action, improvement of hepatic functions, antibacterial and germicidal actions, and the like. However, the effect of Rooibos on prevention or improvement of male climacteric has not been studied.

Female climacteric period refers to a transitional period appearing around the termination of menstruation of a female, and in particular, estrogen secretion does not occur naturally in fat cells thus causing estrogen deficient syndrome. As the estrogen level in the body decreases, pituitary gland produces more follicle stimulating hormone to stimulate ovaries, and most female climacteric symptoms are ascribed to the decrease of estrogen and the increase of follicle stimulating hormone. Female climacteric symptoms may include melancholy, sleep disturbance, bone and muscle pains, palpitation, sweating, facial flushing, amnesia, and the like.

Methods of treating these female climacteric state symptoms may include hormone therapy, estrogen cream, drug formulations, and the like, and the representative method may be the hormone therapy. However, hormone therapy was exhibited to increase breast cancer, stroke, heart attack, phlebothrombosis, cardiovascular diseases, and the like.

Male climacteric is a process that males may experience, such as overall physical and mental deterioration according to the aging of the body. The appearance of neurotic symptoms, anxiety disorder, depression, dizziness, facial flushing, sweating, sleep disturbance, hypotrophy, memory impairment, decrease of work performance ability, decrease of sexual desire, and the like, in male was designated as male climacteric (Werner A A. The male climacteric. J Am Med Assoc 1939; 112: 1441 to 1443). Male climacteric refers to a gradual deterioration in male characteristics, overall physical activities, and feelings influenced by decrease in male hormones. As in females, climacteric period also begins in men at their early 50s and more frequently occurs with the increase in age, accompanying symptoms such as deterioration in the functions of adrenal secretion, fertilizing capacity of sperms, Leydig cells, and decrease in the level of blood serum testosterone thereby expressing male climacteric symptoms. According to the International society for the study of the aging male (ISSAM), the decrease in male hormones lead to decrease in sexual desire, erectile dysfunction, depression accompanying melancholy and annoyance, memory deficit, decrease of the amount of overall fats, decrease of body hair, skin aging, decrease of bone density, increase of visceral fat, and the like (The Korean Association for Sexology; the $1^{st}$ Educational Program for Sex Therapy for Doctors, November 2003). Since the main causes of male climacteric are known to be deterioration in endocrine system in addition to environmental factors, supplement of male hormones has been the major therapy for treating the male climacteric. The therapeutic methods of supplementing male hormones include oral formulations, formulations for skin application, patch formulations, injections, and the like.

However, the treatment of male climacteric disorder via male hormone therapy may increase the prostate gland to further increase the size of prostate cancer, or entail adverse reactions such as aggravation of sleep apnea, incidence of gynecomastia, polycythemia, increase of the risk of cardiovascular disease, and the like.

Furthermore, since the hormone therapy cannot be considered as a principal care of the main cause of climacteric disorders, keen attention should be paid to its prevention.

Accordingly, there is an urgent need for the development of a natural product-derived composition for the prevention and improvement of climacteric disorder, with few adverse reactions.

SUMMARY

An aspect of the present disclosure is to provide a method of preventing, improving, or treating male climacteric or climacteric-related diseases or symptoms including administering an effective amount of a composition including a dandelion extract to a subject in need thereof.

DETAILED DESCRIPTION

Figure 1:
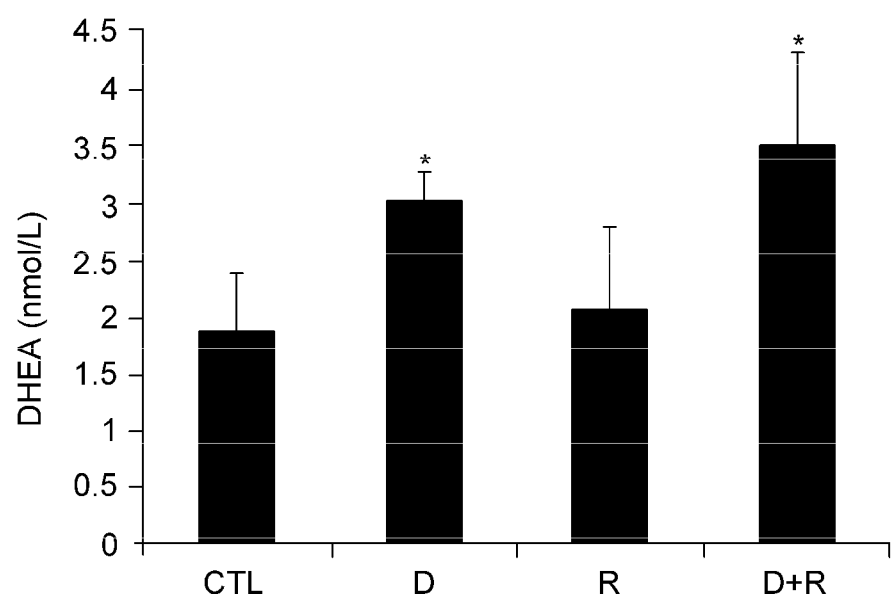
FIG. 1 exhibits the result of quantitative measurement of the amount of dehydroepiandrosterone (DHEA) secretion in mice increased by the administration of the dandelion extract and the composite extract of dandelion and Rooibos (CTL: control group, D: a dandelion extract, R: a Rooibos extract, M+R: a mixed composition of a dandelion extract and a Rooibos extract).

Hereinafter, embodiments of the present disclosure will be described in more detail with reference to the accompanying drawings. In the following description, it should be noted that the same elements are designated by the same reference numerals if possible although they are shown in different drawings. Further, a detailed description of known functions and configurations incorporated herein will be omitted when it may make the subject matter of embodiments according to the present disclosure rather unclear.

The present disclosure relates to a novel use of a dandelion extract and a Rooibos extract, and more specifically, a food composition and a pharmaceutical composition for preventing and improving climacteric, including a dandelion extract, or a dandelion and Rooibos composite extract as an active ingredient.

The present disclosure has been made in an effort to provide a novel natural component with excellent effects of preventing and improving climacteric disorder, and confirms that a dandelion extract increases the level of sex hormones in the body thereby capable of improving and treating climacteric disorder, and also the treatment of the dandelion extract in combination with a Rooibos extract exhibits a synergistic effect, thereby completing the present disclosure.

Accordingly, an object of the present disclosure is to provide a food composition for preventing or improving climacteric or climacteric-related diseases or symptoms thereof including a dandelion extract as an active ingredient.

Another object of the present disclosure is to provide a pharmaceutical composition provides a pharmaceutical composition for preventing or treating male climacteric or male climacteric-related diseases or symptoms thereof including a dandelion extract as an active ingredient.

Still another object of the present disclosure is to provide a food composition for preventing or improving climacteric or climacteric-related diseases or symptoms thereof including a composite extract of dandelion and Rooibos as an active ingredient.

Still another object of the present disclosure is to provide a pharmaceutical composition provides a pharmaceutical composition for preventing or treating climacteric or climacteric-related diseases or symptoms thereof including a composite extract of dandelion and Rooibos as an active ingredient.

Still another object of the present disclosure is to provide a method of preventing, improving, or treating male climacteric or male climacteric-related diseases or symptoms.

In order to achieve the above aspects, in some embodiments, the present disclosure provides a food composition for preventing or improving climacteric or climacteric-related diseases or symptoms thereof including a dandelion extract as an active ingredient.

In order to achieve another aspect, in some embodiments, the present disclosure provides a pharmaceutical composition for preventing or treating male climacteric or male climacteric-related diseases or symptoms thereof including a dandelion extract as an active ingredient.

In order to achieve still another aspect, in some embodiments, the present disclosure provides a food composition for preventing or improving climacteric or climacteric-related diseases or symptoms thereof including a composite extract of dandelion and Rooibos as an active ingredient.

In order to achieve still another aspect, in still another exemplary embodiment, the present disclosure provides a pharmaceutical composition for preventing or treating climacteric or climacteric-related diseases or symptoms thereof including a composite extract of dandelion and Rooibos as an active ingredient.

In order to achieve still another aspect, in still another exemplary embodiment, the present disclosure provides a method of preventing, improving, or treating male climacteric or climacteric-related diseases or symptoms including administering an effective amount of a composition including a dandelion extract to a subject in need thereof.

The present disclosure is further described in detail herein below.

The composition of the present disclosure may include a dandelion extract or a composite extract of dandelion and Rooibos as an active ingredient, and may be used for preventing, improving, and treating climacteric or climacteric-related diseases or symptoms.

The dandelion (*Taraxacum platycarpum* Dahlst.) is a perennial plant in the Family Asteraceae, belonging to Class Dicotyledons, Phylum Angiosperms, and is distributed in China, Japan, Korea, and the like.

The floral axis comes out in summer and a yellow flower blooms at the end of summer People in Korea eat young and soft leaves as vegetables, and western dandelion leaves are used as salad in Europe, and its roots are often used as coffee substitute in New Zealand.

Dandelion leaves are abundant in vitamins A, E, C, and the like, and also include plenty of inorganic components such as potassium, calcium, and iron. In herbal medicine, the entire plant is used as a herbal drug called *Taraxacum platycarpum*, and is known effective for the treatment of swelling, mastitis, laryngopharyngitis, appendicitis, peritonitis, acute hepatitis, and jaundice, and is also used for treating a symptom of urination problem due to high fever.

An injection liquid of dandelion has relatively strong antibacterial effects against resistant strains of *Staphylococcus aureus* and hemolytic *Streptococcus* sp. When administered orally in mice, dandelion can be readily absorbed and exhibit antibacterial activities (Oriental Medicine Encyclopedia, Kyunghee Univ. Press, p. 514 to 515, 1999).

Rooibos (*Aspalathus linearis* (Burm. f.) R. Dahlgren.) is a coniferous tree endemic to part of the Cederberg Mountains of northern Cape Town of South Africa. The plant Rooibos is a shrub-like plant having stems with soft bark in the middle, in which hard branches spring out in a few directions from the area near to the soil, and is hung singly at distances of some 10 mm or in bundles around the adjacent soft needle-like leaves along with thin, slender branches. The height of Rooibos grown in nature varies from 1 m to 1.5 m, and by the harvest time after cultivation, its height reaches ranging from 0.5 m to 1.5 m. Rooibos includes protein, various minerals, iron, manganese, calcium, vitamin C, and the like, in a balanced manner, and is abundant with flavonoid-based antioxidants such as quercetin and polyphenol thus having an antioxidant effect. Reportedly, Rooibos is known to improve skin diseases, treat allergic symptoms and urination problems, improve hepatic functions, relieve constipation, have anticancer and antiviral effects, improve diabetes, have antistress, and the like.

The dandelion extract or the Rooibos extract of the present disclosure may be obtained using an extraction method for natural substances. Preferably, the extraction may be performed using a solvent selected from the group consisting of water, a $C_{1-6}$ organic solvent, and a subcritical or supercritical fluid. The $C_{1-6}$ organic solvent may be one selected from the group consisting of a $C_{1-6}$ alcohol, acetone, ether, benzene, chloroform, ethyl acetate, methylene chloride, hexane, cyclohexane, and petroleum ether.

The solvent used in the present disclosure may be water, a $C_{1-6}$ alcohol, or a mixture thereof, wherein the $C_{1-6}$ alcohol may be ethanol. Preferably, the amount of solvent may vary depending on the amount of dandelion or Rooibos to be extracted, preferably 1 to 20 times volumes of the weight of dandelion or Rooibos, and more preferably, 3 to 10 times volumes of the weight of dandelion or Rooibos.

The extraction temperature of the present disclosure is not particularly limited, but it may be, for example, from 0° C. to 120° C., and preferably 50° C. to 100° C. The extraction time of the present disclosure is not particularly limited, but it may be, for example, from 1 to 10 hours, and preferably from 2 to 6 hours.

The extraction of the present disclosure may be performed by a known method of extracting a natural substance, for example, cold-immersion extraction, hot-water extraction, ultrasonic extraction, or reflux-cooling extraction, and preferably by hot-water extraction or reflux-cooling extraction, and may be repeatedly performed 1 to 10 times, and preferably 2 to 7 times.

The extract of the present disclosure may be filtrated and used in a liquid state, preferably, after solidification via spray drying or freeze-drying, and more preferably, may be dried by mixing with dextrin before spray drying or freeze-drying.

The dandelion extract of the present disclosure may further include a fermentation process before the drying process. The effect of the dandelion extract of the present disclosure on the male climacteric may be improved further by the fermentation process. The fermentation process of the dandelion extract of the present disclosure may be performed by a known fermentation method, and the fermentation bacteria, although not particularly limited, may be lactic acid bacteria, and preferably, *Bifidobacterium longum* or *Lactobacillus acidophilus, Lactobacillus bulgaricus* or *Sterptococcus thermophiles* or *Bifidobacterium infantis* or *Lactobacillus casei* or *Lactobacillus Plantarum* or a mixed bacteria of these lactic acid bacteria. The fermentation condition may vary depending on the kind of bacteria, for example, fermentation may be performed for 24 to 72 hours, preferably 36 to 48 hours at 20° C. to 48° C., and then sterilized, filtrated, concentrated, and then subjected to the drying process to be solidified.

The composition of the present disclosure including a composite extract of dandelion and Rooibos is characterized in that the composition includes both the dandelion extract and the Rooibos extract. The ratio between the dandelion extract and the Rooibos extract, although not particularly limited, may be preferably in the range of from 10:1 to 1:10, more preferably from 9:1 to 6:4, and most preferably from 9:1 to 8:2.

The dandelion extract or the composite extract of dandelion and Rooibos of the present disclosure have an effect of improving male and female sex hormones.

Preferably, the male or female sex hormone may be DHEA family (DHEA, DHEA-s), testosterone (total testosterone-TT, free testosterone-FT, bioavailable testosterone-BF), estradiol (total estradiol-TE, free estradiol-FE, bioavailable estradiol-BE), and sex hormone binding globulin (SHBG).

In some embodiments of the present disclosure, male and female rats, which were fed with the dandelion extract or the composite extract of dandelion and Rooibos, for two months were measured of their DHEA, DHEA-sulfate (DHEA-s), and SHBG concentrations in the blood. As a result, it was confirmed that the rats, fed with the dandelion extract or the composite extract of dandelion and Rooibos, exhibited an increase in the DHEA level in the blood by about 1.14 nmol/L and 1.58 nmol/L, respectively, compared to the control group of rats, and the DHEA-s level was also increased by about 9.58 nmol/L and 15.01 nmol/L, respectively. However, SHBG level was decreased by about 1.6 nmol/L and 2.4 nmol/L, respectively.

Additionally, the blood testosterone level of the male rats and the blood estradiol level of female rats, both fed with a mixed extract for two months, were measured respectively, and the result exhibited that the male rats, which were fed with the dandelion extract or the composite extract of dandelion and Rooibos, exhibited an increase in the blood testosterone level by about 42% and 62%, respectively, whereas the value of bioavailable-testosterone (BT), which is a bioactive form of testosterone, was increased by about 53% and 72%, respectively. Additionally, the blood estradiol level of the female rats, which were fed with the dandelion extract or the composite extract of dandelion and Rooibos, was measured and the result exhibited that the blood estradiol level was increased by about 31% and 47%, respectively, whereas the value of bioavailable-estradiol (BE), which is a bioactive form of estradiol, was increased by about 43% and 61%, respectively.

In another exemplary embodiment of the present disclosure, middle-aged men and women were administered with the dandelion extract or the composite extract of dandelion and Rooibos, and the improvement in the blood testosterone level of men and the blood estradiol level of the women were measured, respectively. As a result, it was exhibited that the blood testosterone level of the middle-aged men administered with the dandelion extract or the composite extract of dandelion and Rooibos was increased by about 8.42% and 18.32%, respectively. Additionally, the blood estradiol level of the middle-aged women was increased by about 11.65% and 24.65%, respectively.

Meanwhile, the dandelion extract or the composite extract of dandelion and Rooibos of the present disclosure have excellent effects of preventing, improving, and treating male and female climacteric-related diseases or symptoms.

The climacteric or climacteric-related diseases or symptoms may be all the diseases or symptoms caused by the male and female sex hormone deficiency, preferably at least one disease or symptom selected from the group consisting of testosterone deficiency syndrome, estrogen deficiency syndrome, sex hormone precursor(DHEA) deficiency syndrome, a disease of increased level of sex hormone binding globulin, neurotic symptoms, anxiety disorder, depression, dizziness, facial flushing, sweating, sleep disturbance, hypotrophy, memory impairment, deterioration in work performance, hypoactive sexual desire disorder, erectile dysfunction, decrease of sperm motility, decrease of stamina, decrease of physical performance, decrease of exercise ability, decrease of body hair, skin aging, decrease of bone density, and an increase of visceral fat, and more preferably, at least one disease or symptom selected from the group consisting of testosterone deficiency syndrome, estrogen deficiency syndrome, sex hormone precursor(DHEA) deficiency syndrome, and a disease of increased level of sex hormone binding globulin.

In another exemplary embodiment of the present disclosure, a questionnaire was conducted regarding Aging Males' Symptom (AMS) and Androgen Deficiency in Aging Males (ADAM), which represent male climacteric and aging. As a result, the group administered with the composite extract of dandelion and Rooibos exhibited an improvement of 31% of male climacteric in AMS questionnaire, and a decrease of 28% of male climacteric in the prevalence rate in ADAM questionnaire. The Aging Males' Symptom (AMS) questionnaire, developed in German language in 1999 by Heinemann et al. (Heinemann L A J, Zimmermann T, Vermeulen A, Thiel C. *A New 'Aging Male's Symptom' (AMS) Scale. The Aging Male* 1992, 2:105 to 114), was a device with validity and reliability designed for the objective evaluation of the effect of aging on men's quality, and its Korean translated version by KIM Se-Hyun in 2003 was exhibited to have validity and reliability (Daig I, Heinemann L A, Kim S et al. *The Aging Males' Symptoms (AMS) scale: review of its methodological characteristics. Health Qual Life Outcomes* (2003) 1:77; LEE, Gil-Hyung, et al., *Korean J Fam Med.* (2010) 31:613 to 621). The Androgen Deficiency in Aging Males (ADAM) questionnaire is a diagnosis sheet developed by Morley et al. in 2000 (Morley J E, Charlton E, Patrick P, Kaiser F E, Cadeau P, McCready D, et al. *Validation of a screening questionnaire for androgen deficiency in aging males. Metabolism* 2000, 49: 1239 to 1242) for the evaluation of male hormone deficiency by confirming 10 representative symptoms based on their clinical experiences, and its validity was confirmed as a diagnostic test to distinguish the state of male hormone deficiency of men in their 40s. Due to not-too-many question items and high sensitivity in the diagnosis, the test is frequently used as a test for distinguishing male hormone deficiency. The Korean version ADAM test sheet is a test sheet of the English version translated into Korean language to be used for selecting male climacteric patients and using them in the clinical studies by KIM, Soo-Woong et al. (KIM, Soo-Woong, O H, Seung-Jun, PAIK, Jae-Seung, KIM, Se-Chul. Development of a Korean Translated Version of Androgen Deficiency in Aging Males (ADAM) Questionnaire sheet. The Korean Urological Association, 2004, 45(7):674 to 679).

Additionally, in another exemplary embodiment, the Menopause rating scale (MRS) questionnaire, which represents female climacteric and aging, was conducted. As a result, the group administered with the composite extract of dandelion and Rooibos exhibited an improvement of 4.47 points in an MRS questionnaire compared to the state before administration.

The Kupperman index in the Menopause rating scale (MRS) questionnaire published in 1953 by Kupperman et al. is a standard for self-questionnaire that has been most frequently used in evaluating studies associated with female climacteric symptoms. This method was remedied by Hildich et al. in 1992 into the Menopause-specific Quality of Life questionnaire (MENQOL), and remedied again in 1996 into the MRS, the new method of measurement. MRS has been cited in many global studies and acknowledged of its reliability and validity.

The MRS method consists of a total of 11 question items including physical symptoms, mental symptoms, and urogenital symptoms, and has an advantage in that the questionnaire is convenient due to a few question items and simplicity.

Accordingly, the present disclosure provides a food composition for preventing and improving climacteric or climacteric-related diseases or symptoms thereof including a dandelion extract as an active ingredient.

Additionally, the present disclosure provides a pharmaceutical composition for preventing and treating male climacteric or male climacteric-related diseases or symptoms thereof including a dandelion extract as an active ingredient.

Additionally, the present disclosure provides a food composition for preventing and improving climacteric or climacteric-related diseases or symptoms thereof including a composite extract of dandelion and Rooibos as an active ingredient.

Additionally, the present disclosure provides a pharmaceutical composition for preventing and treating climacteric or climacteric-related diseases or symptoms thereof including a composite extract of dandelion and Rooibos as an active ingredient.

The food composition of the present disclosure may include processed forms of all natural sources including foods, functional foods, nutritional supplements, health foods, food additives, and the like. This type of food composition may be prepared in various forms according to the conventional method known in the art.

For example, as health foods, the dandelion extract or the composite extract of dandelion and Rooibos may be prepared and served in the form of a tea, a juice, and a drink, or granulated, capsulated, or powdered to be taken. Additionally, the dandelion extract or the composite extract of dandelion and Rooibos may be prepared in the form of a composition by mixing with an active ingredient, which is known to have an effect of preventing or improving diseases induced by climacteric or symptoms thereof.

Additionally, for foods, the dandelion extract or the composite extract of dandelion and Rooibos may be added to drinks (including alcoholic beverages), fruits and process foods thereof (for example, canned fruits, bottled foods, jams, marmalade, and the like), fishes, meats and processed foods thereof (for example, hams, sausage corn beef, and the like), breads and noodles (for example, udons, buckwheat noodles, ramens, spaghetti, macaroni, and the like), fruit juices, various drinks, cookies, taffies, dairy products (for example, butter, cheese, and the like), edible vegetable oils, margarine, vegetable proteins, retort foods, frozen foods, various seasonings (for example, bean paste, soy sauce, sauces, and the like) to be prepared. Additionally, the dandelion extract or the composite extract of dandelion and Rooibos may be prepared and used in the form of powder or concentration to be used as food additives.

Preferably, the dandelion extract or the composite extract of dandelion and Rooibos may be in the amount of 0.001 wt % to 50 wt % relative to the amount of the total food composition, and preferably, 0.1 wt % to 30 wt %.

The pharmaceutical composition of the present disclosure may include a pharmaceutically effective amount of the dandelion extract or the composite extract of dandelion and Rooibos alone, or in combination with at least one pharmaceutically acceptable carrier, excipient, or diluent. As used herein, the term "pharmaceutically acceptable" refers to a non-toxic composition, which is physiologically allowed and does not inhibit the actions of active ingredients when administered to humans, and also does not generally incur allergic reactions such as gastric disorder, dizziness, or similar reactions thereof.

Examples of the carrier, excipient, and diluents may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. Additionally, the pharmaceutical composition may further include a filler, an anticoagulant, a lubricant, a humectant, a flavoring agent, an emulsifying agent, a preserving agent, and the like.

As used herein, the term "effective amount" refers to an amount which exhibits a response greater than that of negative control, and preferably, an amount which is sufficient to exhibit an effect of preventing or treating the disease(s) induced by climacteric or symptoms thereof. The pharmaceutically effective amount of the dandelion extract or the composite extract of dandelion and Rooibos according to the present disclosure may be in the range of from 0.01 mg/day/kg to 100 mg/day/kg of body weight. However, the pharmaceutically effective amount may vary appropriately depending on various factors including the type of a patient, severity of the disease, age, body weight, health state, sex of the patient, administration route, duration of administration, and the like.

The pharmaceutical composition of the present disclosure may be formulated using a method known in the art, in order to provide a rapid, long-acting, or sustained release of active ingredient(s) after administration. The formulation may be prepared in the form of powder, granules, tablets, emulsions, syrups, aerosols, soft or hard gelatin capsules, sterile injection solutions, and sterile powder.

The pharmaceutical composition of the present disclosure may be administered orally or parenterally, although not limited thereto. Examples of the parenteral administration include various routes including, for example, intradermal, intranasal, intraperitoneal, intramuscular, and intravenous administrations.

The pharmaceutical composition of the present disclosure may be administered in combination with a known compound, which is known to have an effect of preventing or treating diseases induced by climacteric, climacteric-related diseases, or symptoms thereof.

Accordingly, the dandelion extract or the composite extract of dandelion and Rooibos according to the present disclosure may be usefully applied to foods and pharmaceutical drugs for preventing, improving, and treating climacteric, climacteric-related diseases, or symptoms thereof in both men and women.

The present disclosure is further described in detail herein below. However, the examples provided herein are for illustrative purposes only and should not be construed as limiting the scope of the present disclosure.

EXAMPLE 1

Preparation of a Dandelion Extract, a Rooibos Extract, and a Composite Extract of Dandelion and Rooibos <1-1> Preparation of a Dandelion Extract Dandelion was selected, pulverized, and extracted via hot-water extraction for about 4 hours using about 7 times volumes (w/v %) of distilled water as a solvent, and then extracted again by adding 4 times volumes of distilled water. The extract was filtrated, concentrated under vacuum, mixed at 1:1 ratio with dextrin, and dried via spray-drying or freeze-drying to obtain a dandelion extract.

<1-2> Preparation of a Rooibos Extract

Rooibos was selected, pulverized, and extracted via hot-water extraction for more than 2 hours using about 8 times volumes (w/v %) of distilled water as a solvent relative to the weight of the pulverized Rooibos, and then extracted again by adding 4 times volumes of distilled water. The extract was filtrated with a filter cloth, and the filtrate was concentrated under vacuum, and the extract was mixed with dextrin at 3:7 ratio, and dried via spray-drying or freeze-drying to obtain a powdered extract.

<1-3> Preparation of a Composite Extract of Dandelion and Rooibos

The powdered dandelion extract and the powdered Rooibos extract respectively obtained in Examples were mixed at 9:1 or 8:2 ratio to prepare a composite extract of dandelion and Rooibos.

TEST EXAMPLE 1

Increase of Sex Hormone Precursors DHEA and DHEA-s, and Sex Hormones Testosterone and Estradiol, and Decrease of Sex Hormone In Vivo Activity-suppressing Globulin (SHBG)

The effects of the composition of the present disclosure on the blood concentration of sex hormone precursors DHEA and DHEA-s, sex hormones testosterone and estradiol, and sex hormone in vivo activity-suppressing globulin (SHBG) in the blood in men and women were examined, in order to observe its effect on the increase of sex hormones in men and women.

<1-1> Effect of Sex Hormone Increase in Rats by the Administration of the Composition of the Present Disclosure Sprague-Dawley-lineage rats (Samtako, Korea) with a body weight of about 250 g were divided into a control group not fed with anything and an experimental group fed with the compositions of the present disclosure (compositions of Examples 1-1 to 1-3), and six rats (three male rats and three female rats) from each group were used in the experiment. During the breeding period, the rats in the experimental group were given ad libitum access to solid feeds for rats and distilled water, and at the same time every morning, were orally administered with the dandelion extract (Example 1-1) or a composite extract of dandelion and Rooibos (Example 1-3; a mixed ratio of 8:2) dissolved in saline at a concentration of 10 mg/kg, whereas the rats in the control group were orally administered with an equal amount of saline for two months. The rats were fasted 8 hours after the final oral administration, anesthetized with ether, and their bellies were cut up to collect blood samples from abdominal vein. The collected blood samples were transferred into heparin-treated tubes, and centrifuged at 2,500 rpm (4° C.) for 15 minutes to separate blood sera. The sexual hormone contents of DHEA, DHEA-s, SHBG, testosterone, and estradiol in the separated blood sera were measured using an ELISA kit (ADI-901-093, 065, 174; Enzo Life Sciences, USA) according to the manufacturer's manual.

The results are exhibited in terms of (mean±standard deviation), and for the verification of significance, the statistic handling was conducted using the Student's t-test, and indicated with the significance of $p<0.05$. The results are illustrated in FIGS. 1 to 7.

The measurement results revealed that, as illustrated in FIG. 1, the rats fed with the dandelion extract (D) and the Rooibos extract (R), respectively, exhibited an increase in the level of blood DHEA by about 1.2 nmol/L and 0.2 nmol/L, respectively, compared to the control group (CTL).

Figure 2:
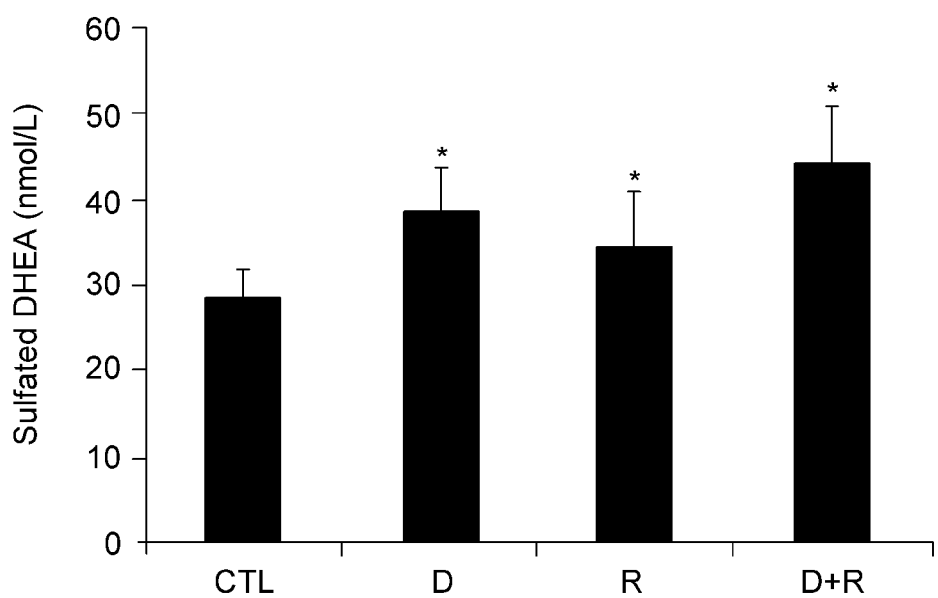
FIG. 2 exhibits the result of quantitative measurement of the amount of DHEA-s secretion in mice increased by the administration of the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 2, the DHEA-s value was increased about 9 nmol/L and 5 nmol/L, respectively. And, as illustrated in FIGS. 1 and 2, when the rats were fed with the mixture (D+R), the DHEA and sulfated DHEA values increased close to 1.6 nmol/L and 15 nmol/L, respectively, compared to the control group (CTL).

Figure 3:
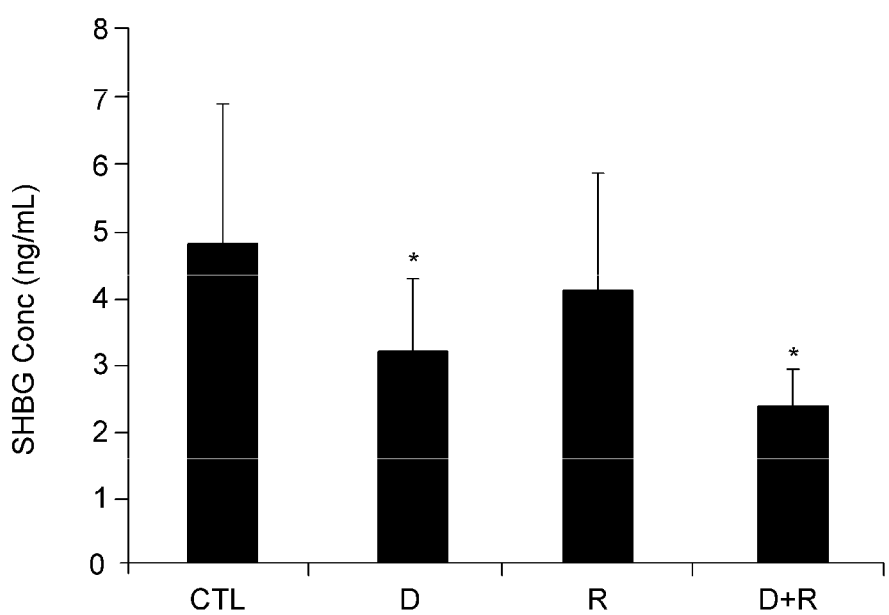
FIG. 3 exhibits the result of measurement of the blood concentration of SHBG in mice decreased by the administration of the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 3, the rats fed with the dandelion extract (D) and the Rooibos extract (R), respectively, exhibited a decrease of about 1.6 nmol/L and 0.7 nmol/L in blood concentration of SHBG, compared to the control group (CTL), whereas when the rats were fed with the mixture (D+R), the SHBG value decreased significantly by about 2.4 nmol/L, compared to the control group (CTL).

Figure 4:
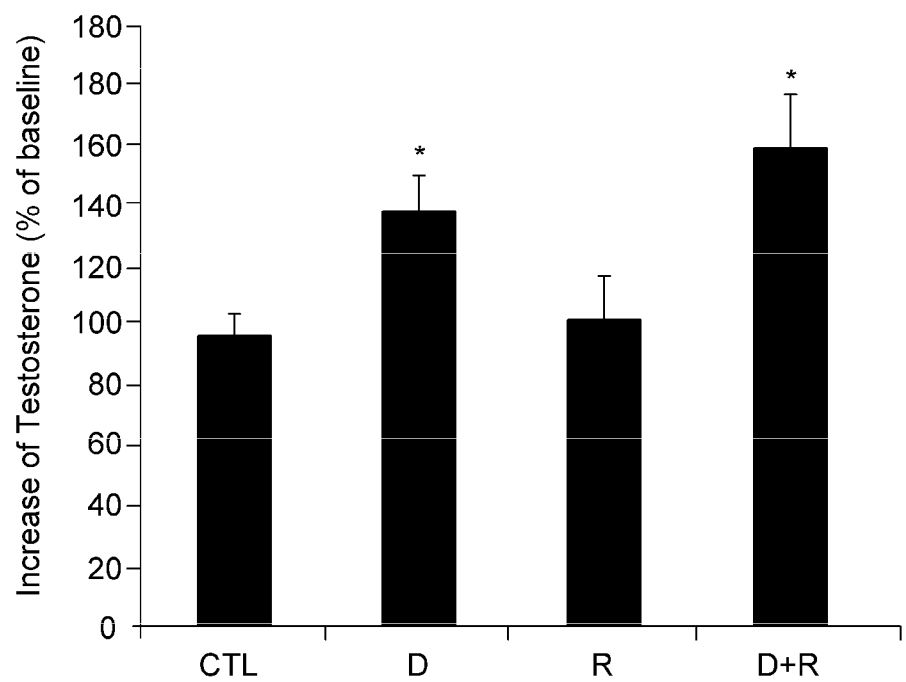
FIG. 4 exhibits the result of the increased amount of the total testosterone (TT, total testosterone) in the blood in male mice increased by the administration of the dandelion extract and the composite extract of dandelion and Rooibos, compared to that before feeding with the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 4, the male rats fed with the dandelion extract (D) and the Rooibos extract (R), respectively, exhibited an increase of about 38% and 2% in the total testosterone (TT) value in the blood, respectively, compared to the control group (CTL).

Figure 5:
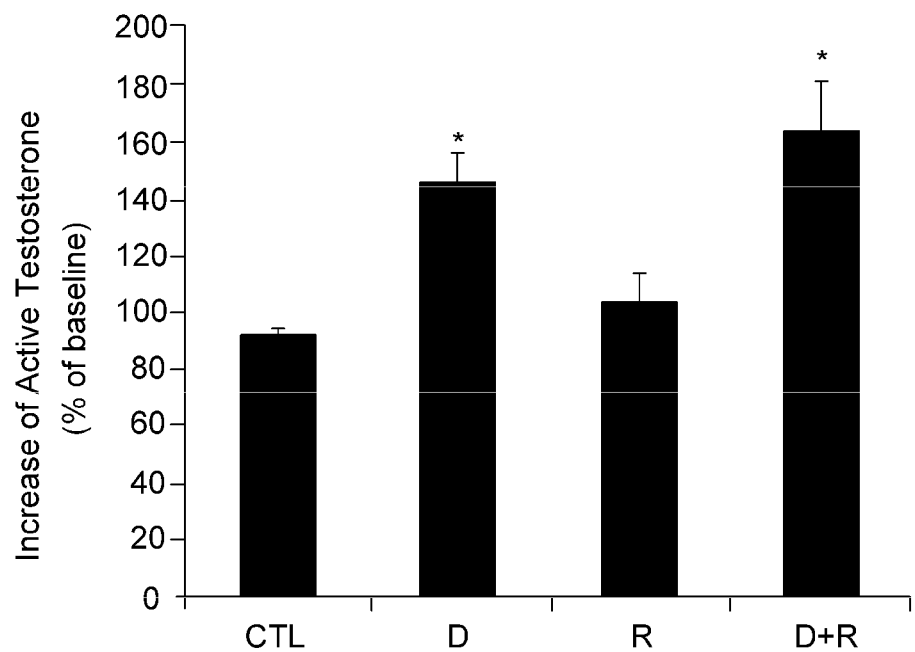
FIG. 5 exhibits the result of the increased amount of the total testosterone in an active form (BT, bioavailable testosterone) in the blood in male mice increased by the administration of the dandelion extract and the composite extract of dandelion and Rooibos, compared to that before being fed with the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 5, the rats fed with the dandelion extract (D) and the Rooibos extract (R), respectively, exhibited an increase in the bioavailable testosterone (BT) value in the blood by about 45% and 4%, respectively. And, as illustrated in FIGS. 4 and 5, when the rats were fed with the mixture (D+R), the total testosterone (TT) value and the bioavailable testosterone (BT) value in the blood increased significantly by about 58% and 64%, respectively.

Figure 6:
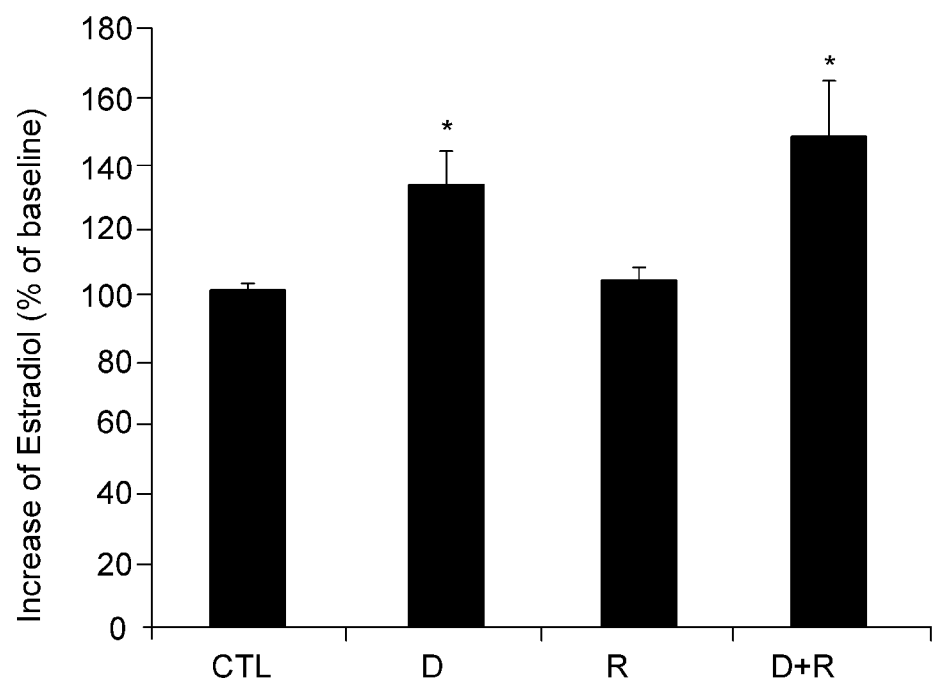
FIG. 6 exhibits the results of the increased amount of the estradiol (TE, total estradiol) and the increased amount of the estradiol in an active form in the blood in female mice increased by the administration of the dandelion extract and the composite extract of dandelion and Rooibos, compared to that before being fed with the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 6, the female rats fed with the dandelion extract (D) and the Rooibos extract (R), respectively, exhibited an increase in the total estradiol (TE) value in the blood by about 33% and 6%, respectively, compared to the control group (CTL).

Figure 7:
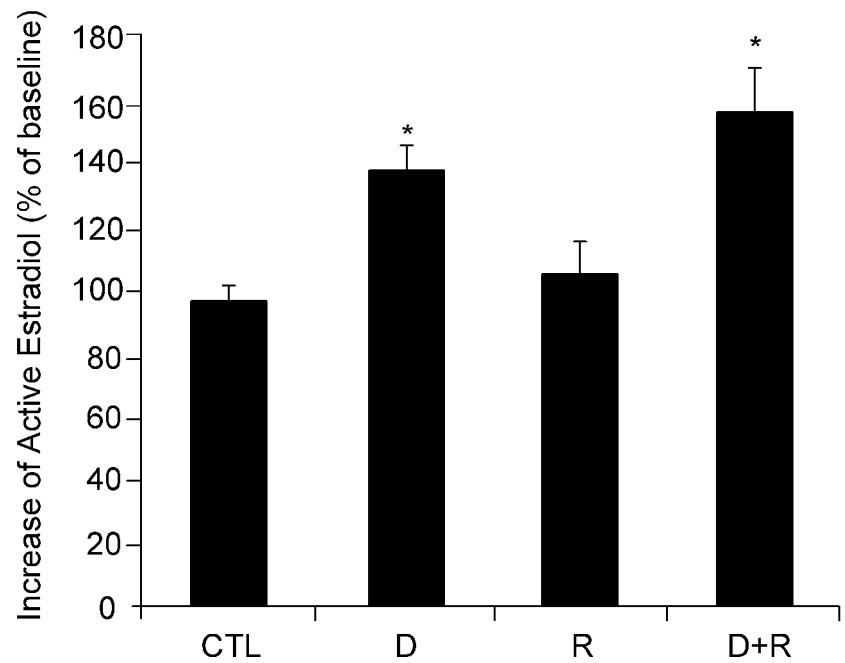
FIG. 7 exhibits the result of the increased amount of the estradiol in an active form (BE, bioavailable estradiol) in the blood in female mice increased by the administration of the dandelion extract and the composite extract of dandelion and Rooibos, compared to that before being fed with the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 7, the rats fed with the dandelion extract (D) and the Rooibos extract (R), respectively, exhibited an increase in the bioavailable estradiol (BE) value in the blood by about 40% and 5%, respectively. And, when the rats were fed with the mixture (D+R), the total estradiol (BT) and the bioavailable estradiol (BE) values in the blood exhibited a significant increase by about 49% and 58%, respectively.

EXPERIMENTAL EXAMPLE 2

Effect of Sex Hormone Increase in the Blood Via Test in Humans

Adult men and women were administered with the compositions of the present disclosure, and the changes in blood concentrations of sex hormone precursors and the male and female sex hormones in the blood and the decrease in SHBG, before and after the administration, were examined thereby confirming the effect of the compositions of the present disclosure on the increase of sex hormones.

<2-1> Subjects of Research and Research Period

Forty middle-aged men aged 40 or more, who agreed to participate on the present experiment, were divided into a control group (placebo), who were administered with a placebo drug, and an experimental group, who were administered with the dandelion extractor the mixture of the dandelion extract and the Rooibos extract (D+R; 1:9 mixed ratio), randomly assigning 10 people per each group for a period of four weeks to be administered with the placebo drug or the experimental drug, in the amount of 400 mg daily. Additionally, forty middle-aged women aged 40 or more were also subjected to an experiment after randomly assigning them in the same manner as in men. Before and after the administration, the blood concentration of sex hormones was examined and the effect of the administration of the compositions of the present disclosure on the increase of sex hormones in men and women were evaluated.

<2-2> Effect of Sex Hormone Increase in the Blood in Both Men and Women Due to the Intake of the Compositions of the Present Disclosure Blood samples were collected at the same time, i.e., 2 pm, before and after the administration, from the brachial veins of men and women in the experimental groups. The collected blood samples were transferred into heparin-treated tubes, and centrifuged at 2,500 rpm (4° C.) for 15 minutes to separate blood sera. The sex hormone contents of testosterone and estradiol in the separated blood sera were measured using an ELISA kit (ADI-901-093, 065, 174; Enzo Life Sciences, USA) according to the manufacturer's manual.

The results are exhibited in terms of (mean±standard deviation), and for the verification of significance, the statistic handling was conducted using the Student's t-test, and indicated with the significance of p<0.05. The results are illustrated in FIGS. 8 and 9.

Figure 8:
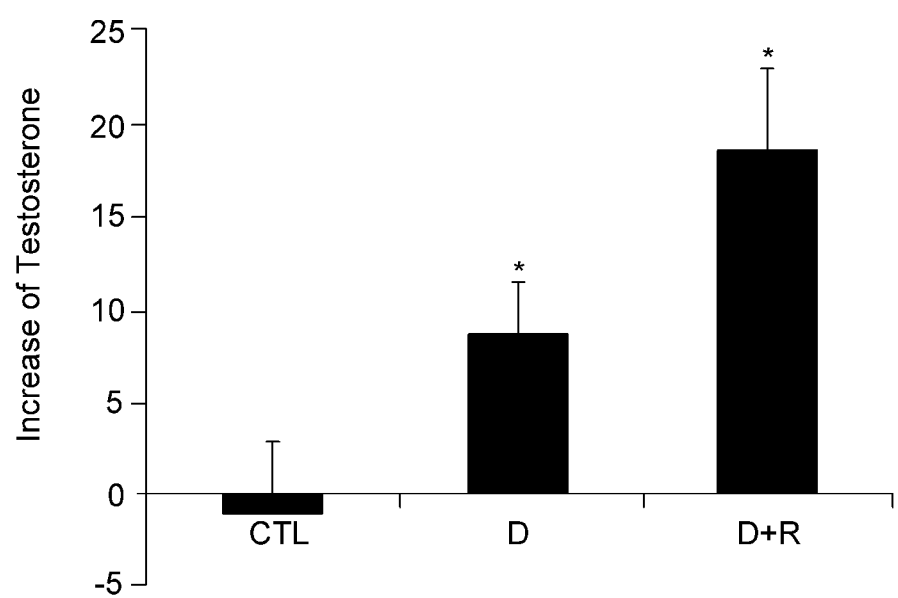
FIG. 8 exhibits the result of the concentration of testosterone, a male sex hormone, in men aged 40 or more, increased by the administration of the dandelion extract and the composite extract of dandelion and Rooibos (CTL: control group, D: a dandelion extract, R: a Rooibos extract, M+R: a mixed composition of a dandelion extract and a Rooibos extract).

The measurement results revealed that, as illustrated in FIG. 8, the men administered with the dandelion extract (D) exhibited an increase in the total testosterone (IT) value in the blood by about 8.4%, respectively, compared to the control group (CTL), whereas the men administered with the mixture (D+R) exhibited an increase in the total testosterone value (IT) in the blood by about 18%.

Figure 9:
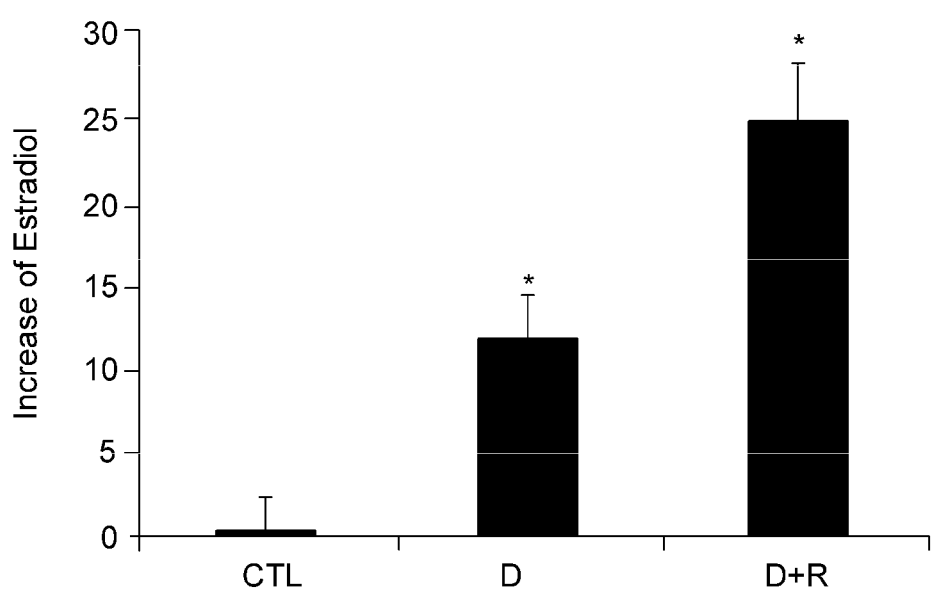
FIG. 9 exhibits the result of the concentration of estradiol, a female sex hormone, in women aged 40 or more, increased by the administration of the dandelion extract and the composite extract of dandelion and Rooibos (CTL: control group, D: a dandelion extract, R: a Rooibos extract, M+R: a mixed composition of a dandelion extract and a Rooibos extract).

Additionally, as illustrated in FIG. 9, the women administered with the dandelion extract (D) exhibited an increase in the total estradiol (TE) in the blood by about 11.6%, compared to the control group (CTL), whereas the women administered with the mixture (D+R) exhibited an increase in the total estradiol (TE) value by about 24.7%, compared to the control group (CTL).

EXPERIMENTAL EXAMPLE 3

Effect of Preventing Male Climacteric Via Test in Humans

Adult men were administered with the compositions of the present disclosure, and the effect of the compositions on the prevention and treatment of male climacteric was examined via male climacteric evaluation questionnaire, before and after the administration.

<3-1> Subjects of Research and Research Period

Fifty middle-aged men aged 40 or more, who agreed to participate on the present experiment, were divided into a control group (placebo), who were administered with a placebo drug, and an experimental group, who were administered with the mixture (D+R; 1:9 mixed ratio), randomly assigning 25 people per each group for a period of four weeks to be administered with the placebo drug or the experimental drug, in the amount of 400 mg daily. Before and after the administration, the blood concentration of sex hormones was examined and the participants were requested to fill out the questionnaire sheets <Test Example 3-2> and <Test Example 3-3>, and the effect of the administration of the compositions of the present disclosure on the male climacteric was evaluated.

<3-2> Korean Version of AMS(Aging Males' Symptom) Scale

The Aging Males' Symptom (AMS) scale, developed in German language in 1999 by Heinemann et al. (Heinemann L A J, Zimmermann T, Vermeulen A, Thiel C. *A New 'Aging Male's Symptom' (AMS) Scale. The Aging Male* 1992, 2:105 to 114), was a device with validity and reliability designed for the objective evaluation of the effect of aging on men's quality, and its Korean translated version by KIM Se-Hyun in 2003 was exhibited to have validity and reliability (Daig I, Heinemann L A, Kim S et al. *The Aging Males' Symptoms (AMS) scale: review of its methodological characteristics. Health Qual Life Outcomes* (2003) 1:77; LEE, Gil-Hyung, et al., *Korean J Fam Med*. (2010) 31:613 to 621). The AMS results regarding the experimental group administered with the compositions of the present disclosure and the control group are listed in Table 1 and illustrated in FIG. 10. The results are exhibited in terms of (mean±standard deviation), and the statistic handling was conducted using the Student's t-test, and indicated with the significance of p<0.05.

Figure 10:
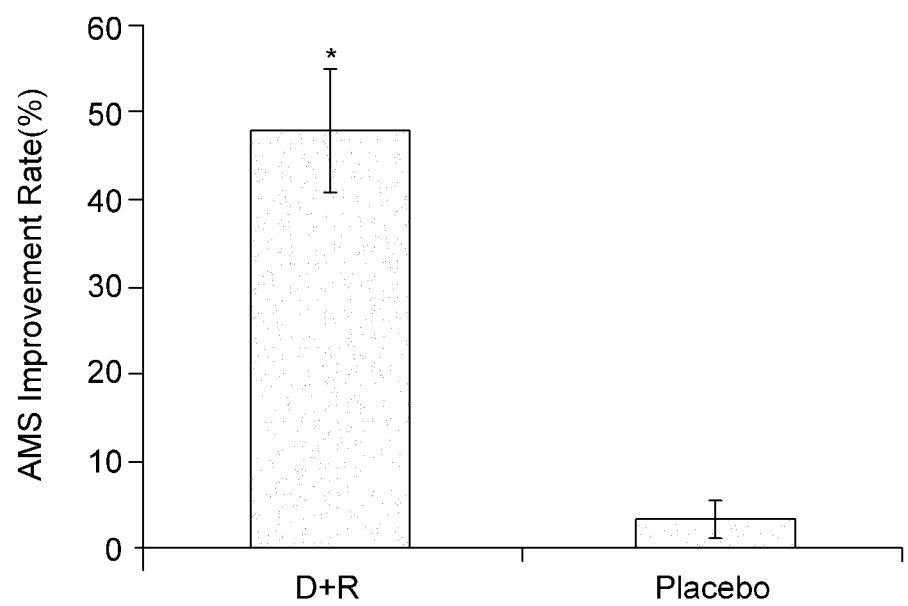
FIG. 10 exhibits the result of male climacteric symptoms improved by the administration of the composite extract of dandelion and Rooibos, the values of which being quantitated after evaluation via AMS questionnaire (placebo (control group), D+R: a mixed composition of a dandelion extract and a Rooibos extract).
Figure 11:
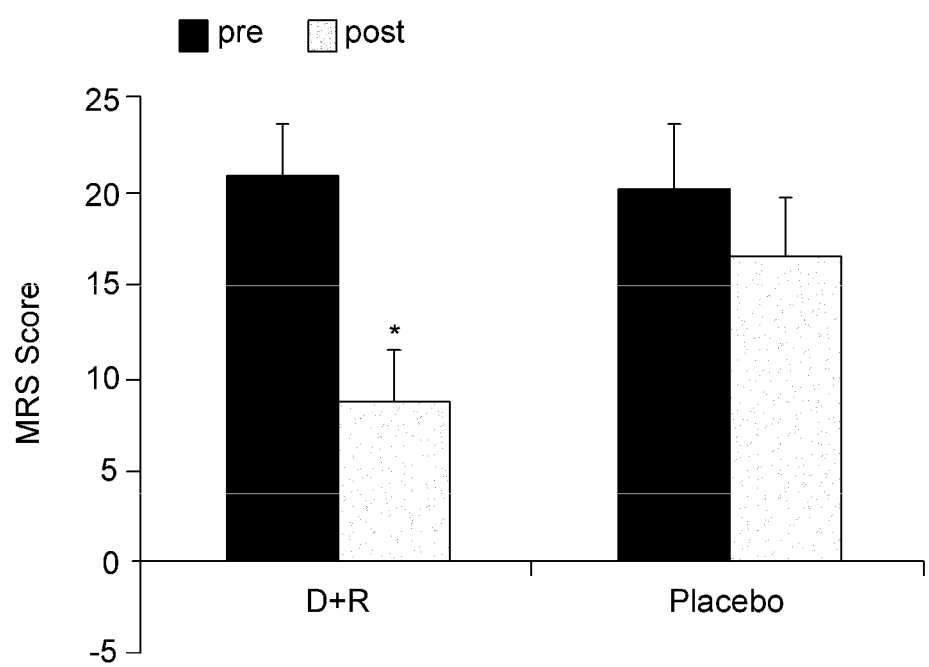
FIG. 11 exhibits the result of female climacteric symptoms improved by the administration of the composite extract of dandelion and Rooibos, the values of which being quantitated after evaluation via MRS questionnaire (placebo (control group), D+R: a mixed composition of a dandelion extract and a Rooibos extract).

The test results, as listed in Table 1 and illustrated in FIG. 10, revealed that there was no significant difference in AMS score in the control group, before and after the administration, whereas the experimental group administered with the compositions of the present disclosure exhibited a decrease in AMS score by about 13 points, thus exhibiting about 31% improvement in male climacteric symptoms. Accordingly, it was confirmed that the compositions of the present disclosure can alleviate the climacteric symptoms appearing in male senescence, in the test items such as improvement in physical activities, sexual desire, stamina, erectile improvement, improvement in sleeping, emotional stability, and the like.

TABLE 1

Result of AMS Evaluation

| AMS Score | Before Administration (score) | After Administration (score) | Improvement of Climacteric (% of before) |
|---|---|---|---|
| Control Group (placebo) | 40.48 ± 8.38 | 37.24 ± 7.13 | 108 |
| Experimental Group (M + R) | 41.41 ± 9.31 | 28.57 ± 6.91* | 131* |

<3-3> Korean Version of Androgen Deficiency in Aging Males (ADAM)

The Androgen Deficiency in Aging Males (ADAM) questionnaire is a diagnosis sheet developed by Morley et al. in 2000 (Morley J E, Charlton E, Patrick P, Kaiser F E, Cadeau P, McCready D, et al. *Validation of a screening questionnaire for androgen deficiency in aging males. Metabolism* 2000, 49: 1239 to 1242) for the evaluation of male hormone deficiency by confirming 10 representative symptoms based on their clinical experiences, and its validity was confirmed as a diagnostic test to distinguish the state of male hormone deficiency of men in their 40s. Due to not-too-many question items and high sensitivity in the diagnosis, the test is frequently used as a test for distinguishing male hormone deficiency. The Korean version ADAM test sheet is a test sheet of the English version translated into Korean language to be used for selecting male climacteric patients and using them in the clinical studies by KIM, Soo-Woong et al. (KIM, Soo-Woong, O H, Seung-Jun, PAIK, Jae-Seung, KIM, Se-Chul. Development of a Korean Translated Version of Androgen Deficiency in Aging Males (ADAM) Questionnaire sheet. The Korean Urological Association, 2004, 45(7):674 to 679). The ten question items in ADAM are to be answered in YES or NO regarding each symptom, and the questionnaire enables to evaluate the deficiency in male hormones by examining the presence of hypogonadism or other symptoms. Among the test items, when the question item no. 1 or 7 is answered "YES", or at least three or more questions items, other than the question item nos. 1 and 7, are answered "YES", the subject may be evaluated to have the male climacteric symptoms.

The ADAM result on the experimental group, who were administered with the compositions of the present disclosure, and the control group, who were administered with the placebo drug, are exhibited in terms of the prevalence rate (%, the percentage of people who complain the presence of male hormone deficiency among the subjects involved in the experiment) of the male climacteric by the ADMS questionnaire sheet, as listed in Table 2 below.

As exhibited in the test result in Table 2, the control group exhibited no significant change in the prevalence rate in male climacteric, evaluated based on the ADAM test sheet, whereas the group administered with the compositions of the present disclosure exhibited a decrease of about 28% in the prevalence rate in male climacteric, evaluated based on the ADAM test sheet after the administration. Accordingly, the compositions of the present disclosure were exhibited to effectively improve the ADAM test items, such as hypoactive sexual desire disorder, erectile dysfunction, vitality, physical strength, exercise ability, quality of life, depression, work performance, and the like, thereby confirming that the compositions of the present disclosure can improve the male climacteric symptoms.

TABLE 2

Result of ADAM Evaluation

| Prevalence Rate of Male Climacteric (%) | Before Administration | After Administration |
| --- | --- | --- |
| Control Group | 82 | 72 |
| Experimental Group | 81 | 53 |

EXPERIMENTAL EXAMPLE 4

Effect of Prevention of Female Climacteric by Test in Human Body

Adult women were administered with the compositions of the present disclosure, and the effect of the compositions on the prevention and treatment of female climacteric caused by the disorder in regulating female hormone was examined via questionnaire sheet for evaluation of the female climacteric, before and after the administration.

<4-1> Subjects and Research Period

Forty middle-aged women aged 40 or more, who agreed to participate on the present experiment, were divided into a control group (placebo), who were administered with a placebo drug, and an experimental group, who were administered with the mixture (D+R; 1:9 mixed ratio), randomly assigning 20 people per each group for a period of four weeks to be administered with the placebo drug or the experimental drug, in the amount of 500 mg daily. Before and after the administration, the participants were requested to fill out the questionnaire sheet <Test Example 4-1>, and the effect of the administration of the compositions of the present disclosure on the female climacteric was evaluated.

<4-2> Korean Version of Menopause Rating Scale (MRS)

The Kupperman index in the Menopause rating scale (MRS) questionnaire published in 1953 by Kupperman et al. is a standard for self-questionnaire that has been most frequently used in evaluating studies associated with female climacteric symptoms. This method was remedied by Hildich et al. in 1992 into the Menopause-specific Quality of Life questionnaire (MENQOL), and remedied again in 1996 into the MRS, the new method of measurement. MRS has been cited in many global studies and acknowledged of its reliability and validity.

This questionnaire has a total of eleven question items including physical symptoms, mental symptoms, urogenital symptoms, and the like, and has an advantage in that it has a few question items and they are simple.

Based on the total score, the score of "0 to 4" points indicates the subject is in a good climacteric state with a smooth life, whereas the score of "5 to 8" points indicates the subject is in a mild climacteric state thus requiring management. The score of "9 to 15" points indicates the subject is in a serious climacteric state having climacteric symptoms thus requiring treatment by a specialist. The score of 16 points or higher indicates that the subject is in an extremely serious climacteric state essentially requiring a long-term plan and treatment of the climacteric.

The test result exhibited, as illustrated in FIG. 12, there was no significant change in MRS score in the control group, before and after the administration, whereas the group administered with the compositions of the present disclosure exhibited a decrease in MRS score by about 4.4 points, thus exhibiting an improvement in the female climacteric symptoms by about 45%.

Accordingly, it was confirmed that the compositions of the present disclosure can alleviate the female climacteric symptoms appearing due to female senescence in MRS test items, such as physical strength, sexual desire, sleeping disorder, mental instability, urogenital problems, joint problems, depression, hypersensitivity, and the like.

As described above, the present disclosure provides a food composition and a pharmaceutical composition for preventing, improving, and treating climacteric, climacteric-related diseases, or symptoms thereof including the dandelion extract or the composite extract of dandelion and Rooibos. The composition of the present disclosure can increase the total level of both male and female sex hormones in the blood, increase the sex hormones in an active form by reduction of SHBG, thus being effective in the prevention and treatment of climacteric, climacteric-related diseases, or symptoms thereof.

Although the embodiments of the present disclosure have been described for illustrative purposes, those skilled in the art will appreciate that various modifications, additions and substitutions are possible, without departing from the scope and spirit of the disclosure. Accordingly, the embodiments disclosed in the present disclosure are merely to not limit but describe the technical spirit of the present disclosure. Further, the scope of the technical spirit of the present disclosure is limited by the embodiments. Accordingly, the protection scope of the present disclosure should be defined by the appended claims, and should be construed to cover all technical ideas that are equivalent thereto.

What is claimed is:

1. A method of reducing the instance of, improving, or treating male climeractic disorder and symptoms thereof comprising:

administering an effective amount of a composition comprising a dandelion extract and a rooibos extract to a subject with male climeractic disorder, wherein the dandelion and rooibos extracts are obtained by extraction with a solvent selected from the group consisting of water, alcohol, and a mixture thereof; wherein the weight ratio of the dandelion extract and the rooibos extract is 4:1-1:9; and wherein the amount of the dandelion extract, or dandelion extract and rooibos extract, administered is from 0.01 mg/day/kg to 100 mg/day/kg of body weight.

2. The method of claim 1, wherein the composition is a food composition.

3. The method of claim 1, wherein the composition is a pharmaceutical composition.

4. The method of claim 1, wherein the solvent is a C1-C6 alcohol.

5. The method of claim 1, wherein the symptoms are at least one selected from the group consisting of testosterone deficiency syndrome, sex hormone precursor (DHEA) deficiency syndrome, a disease of increased level of sex hormone binding globulin, neurotic symptoms, anxiety disorder, anxiety, dizziness, facial flushing, sweating, sleep disturbance, hypotrophy, memory impairment, deterioration in work performance, hypoactive sexual desire disorder, erectile dysfunction, decrease of sperm motility, decrease of stamina, decrease of physical performance, decrease of exercise ability, decrease of body hair, skin aging, decrease of bone density, and increase of visceral fat.

* * * * *